United States Patent [19]
Keller

[11] Patent Number: 4,908,032
[45] Date of Patent: Mar. 13, 1990

[54] RECONSTRUCTION PROSTHESIS

[75] Inventor: Arnold Keller, Kayhude, Fed. Rep. of Germany

[73] Assignee: Waldemar Link GmbH & Co., Hamburg, Fed. Rep. of Germany

[21] Appl. No.: 163,093

[22] Filed: Mar. 2, 1988

[30] Foreign Application Priority Data

Mar. 9, 1987 [DE] Fed. Rep. of Germany ....... 8703491

[51] Int. Cl.⁴ .............................................. A61F 2/30
[52] U.S. Cl. ......................................... 623/18; 623/23
[58] Field of Search ........................ 623/16, 18, 19, 20, 623/21, 22, 23; 128/92 YZ, 92 YF

[56] References Cited

U.S. PATENT DOCUMENTS

| | | | |
|---|---|---|---|
| 2,785,673 | 3/1967 | Anderson | 623/23 |
| 4,077,070 | 3/1978 | Sivash | 623/18 |
| 4,227,518 | 10/1980 | Aginsky | 623/18 |
| 4,549,319 | 10/1985 | Meyer | 623/23 |
| 4,783,192 | 9/1988 | Wroblewski et al. | 623/23 |

FOREIGN PATENT DOCUMENTS

| | | | |
|---|---|---|---|
| 3205577 | 10/1982 | Fed. Rep. of Germany. | |
| 3336005 | 4/1985 | Fed. Rep. of Germany. | |
| 3340767 | 5/1985 | Fed. Rep. of Germany | 623/22 |
| 762871 | 4/1977 | U.S.S.R. | |

Primary Examiner—Richard J. Apley
Assistant Examiner—David J. Isabella
Attorney, Agent, or Firm—Chilton, Alix & Van Kirk

[57] ABSTRACT

A hip prosthesis has a stem which is to be anchored in the femur bone and has a transverse surface for support on a subtrochanteric bone surface. The transverse surface comprises a plurality of support parts which engage in the bone at mutual spacings and which preferably radiate in the form of a star from a ring.

8 Claims, 1 Drawing Sheet

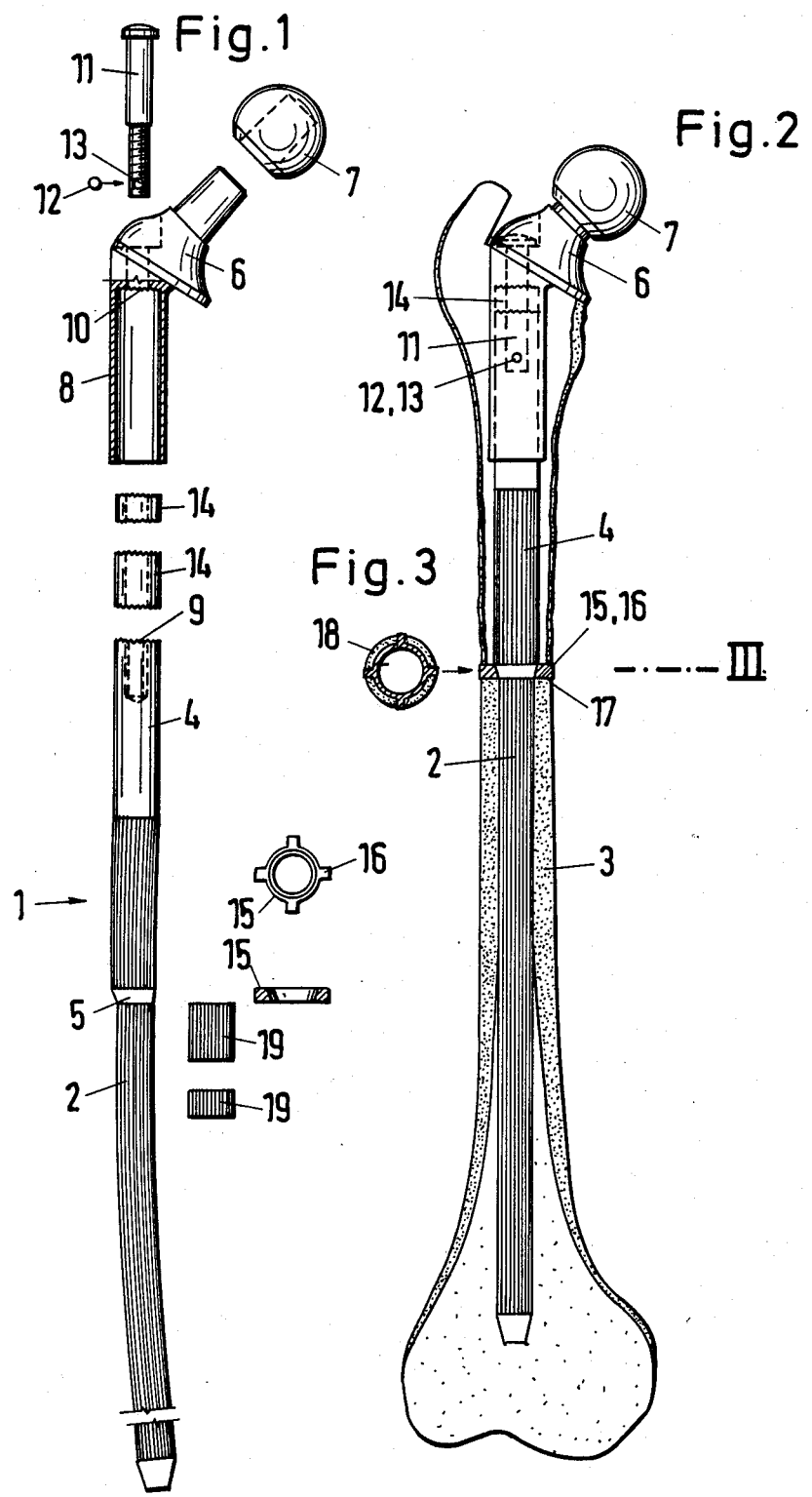

RECONSTRUCTION PROSTHESIS

DESCRIPTION

After implantation of a prosthesis, destruction of the topmost femur section can occur, and this manifests itself in an extremely thin or even partially absent cortical substance. If, in such a state, a reoperation has to be carried out, this section cannot be used for supporting the new prosthesis. For this case, the state of the art makes two prosthesis versions available. One of these versions is based on the replacement of the degenerated, upper section of the femur, which is removed and replaced by a prosthesis. The latter is supported on the resection plane and its stem is anchored in the distal, remaining part of the bone. The disadvantage of this version is the loss of the natural muscular attachment in the trochanter region and the restriction of further prosthetic measures in the future. Not infrequently, this causes total loss of the femur bone. The second, more frequently used version comprises a prosthesis with a long stem, which reaches down beyond the degenerated section of the femur bone and is cemented in deeply in the distal section of the bone. In this case, the disadvantage is that, as a rule, secure support for the neck of the prosthesis resting on the bone in the weakened section of the femur section cannot be achieved. Thus, there is a risk of the prosthesis subsiding into the femur bone. Due to the absence of support of the upper prosthesis part, the latter is subjected to a higher oscillating load and tends to an increased risk of fracture. It has been proved that, for biomechanical and biological reasons, total filling of the degenerated bone section with cement provokes complete failure of the residual remaining, thin cortical substance.

Regeneration of the weakened bone section can be achieved not by cement, but only by a cement-free implantation technique. However, this is to be expected only if there is no movement between the prosthesis and the bone, and this presupposes stable anchorage of the prosthesis in the lower bone section, with prevention of subsidence of the prosthesis.

The invention is based on the object of providing a prosthesis of the type described at the outset, which is better able to meet these aims.

According to the invention, this is achieved when the transverse surface, supported on the bone, of the prosthesis is formed by a plurality of support parts engaging in the bone at mutual spacings. These support parts are advantageously formed such that they radiate in the form of a star from a ring, a sleeve or the like. The interspace formed between the support parts makes it possible for a bone connection to remain or to be reformed between the femur bone sections located below and above the support parts. The invention thus makes it possible for the prosthesis to be supported in a central part of the femur bone, without the upper section having to be completely resected. Rather, the thinned, upper section can be filled with natural, homologous or autologous bone material and thus reinforced, without the hold of the prosthesis having to rely on this bone section.

The support of the prosthesis does not have to be based exclusively on the support parts engaging in the bone at mutual spacings; rather, an annular support surface can also be used, the external diameter of which is smaller than the external diameter of the bone at the particular point. In many cases, it is sufficient if the support parts engaging in the bone at mutual spacings merely lie in one plane; however, the use of support parts in several planes is also possible, for example by means of projections which are arranged like spines of a hedgehog on one or more ring parts.

In the case of the implantation of a ring carrying support parts in one plane, it is possible to introduce the ring after the femur bone has been completely severed at the particular point. The prosthesis stem is then knocked into the medullary canal. The ring is thus positioned essentially within the medullary space, so that linear growth of the cortical substance from the distal side towards the proximal side is subsequently possible similarly as in the case of a fracture. Instead, it may also be possible in some cases first to introduce the stem and to insert the support parts from the outside through the bone and to join them to the prosthesis stem.

If the support parts are located on a part which can be introduced separately from the stem, the stem advantageously comprises a contact surface by means of which it is in turn supported. To adjust the correct position of the prosthesis, spacer rings can be provided which can be inserted between the contact surface of the stem and the part carrying the support parts. For adjustment, provision can also be made for arranging adaptors of adjustable length between a prosthesis part carrying the prosthesis head and the prosthesis part which forms or carries the support parts.

The invention is described below in more detail with reference to the drawing which illustrates an advantageous embodiment example and in which:

FIG. 1 shows the prosthesis in an exploded view of its individual components,

FIG. 2 shows the prosthesis in the inserted state and

FIG. 3 shows a cross-section through FIG. 2 in the plane III.

The prosthesis stem 1 consists of a lower section 2, which is to be introduced into the middle to lower section of the femur bone 3, and of an upper section 4 which has a slightly greater diameter than the lower section 2, so that a tapered contact surface 5 is formed at the transition point by a change in diameter. The section 2 and, if appropriate, parts of the section 1 can have longitudinal grooves for a greater-area joint with the bone material. The upper section 4 of the stem is releasably joined in any desired, known manner to the neck part 6 which carries the prosthesis head 7. In the case shown, the joint is accomplished as a result of the neck part 6 having a sleeve 8 which encloses and fits around the upper stem section 4 for improved transmission of the bending moments. The mutually opposite end faces 9 of the prosthesis stem and 10 of the sleeve bottom have mutually engaging, radial teeth which allow a rotationally secure joint by means of the tension screw 11 in various angular positions, in order to adjust the desired anteversion. The tension screw 11 can be secured against undesired twisting by means of a known locking device 12 in a bore 13. Adaptors 14 allow a desired spacing between the joint head 7 and the contact surface 5 to be set.

In the implanted state, the prosthesis is supported via the contact surface 5 on a support ring 15 which has a bore fitting the contact surface 5 and from which several support parts or ribs 16 radiate as circumferentially spaced apart radial projections. The external diameter of the support ring 15 carrying the support parts 16 is greater than the internal diameter of the medullary canal, but smaller than the external diameter of the femur bone. Therefore, both the support ring and the projections can be supported on the resection surface 17 of the femur bone. At the same time, this leaves sufficient interspace in the form of a plurality of longitudinally extending channels or paths between the support projections in the cross-sectional region of the bone, through which interspace the bone material 18 can connect the upper section and the lower section of the femur bone. Spacer rins or shims 19 are provided for adjusting the distance between the contact surface 5 and the support ring 15.

The operation procedure is such that, at a height at which the cortical substance of the femur bone is of sufficient thickness, the femur bone is severed. The support ring 15 is interposed at this point. The prosthesis stem 1 is then knocked into the medullary canal from the proximal end. The upper, thinned femur section is filled with natural, homologous or autologous bone material, and the neck part 6 is put in place on the prosthesis stem and fixed in the desired anteversion position. The adaptors 14 and/or 19 then allow correct length adjustment. It can be provided that the ring part 15 of the support ring is located predominantly or exclusively within the medullary canal, so that the greatest possible cross-sectional area is left between the support projections 16 for the cortical substance to grow through longitudinally.

As a result of the bone reconstruction achievable according to the invention, measures and re-operations which may become necessary later are facilitated considerably and the risk of total loss of the femur bone is substantially reduced.

I claim:

1. A hip prosthesis to be supported by a transverse subtrochanteric bone surface located intermediate upper and lower portions of the femur bone, comprising:

a stem having upper and lower portions, for positioning longitudinally within respective upper and lower portions of the femur bone;

support means associated with the stem to extend transversely from the stem and between the upper and lower bone portions, the support means having upper and lower bone engaging surfaces and an external diameter sized to be substantially no larger than the external diameter of the bone portions, the lower bone engaging surface being adapted to transfer longitudinal forces from the upper portion of the stem through said bone surface to the lower bone portion, and to define with said upper bone engaging surface a plurality of interspaces for bone growth between the upper and lower bone portions.

2. A prosthesis as claimed in claim 1, wherein the support means is a rigid member separate from the stem (1) and introducible into the bone before the stem.

3. A prosthesis as claimed in claim 1, wherein the support means includes a ring, and the interspaces are defined by ribs radiating in the form of a star from the ring (15).

4. A prosthesis as claimed in claim 3, wherein the stem (1) includes a contact surface (5) which interacts with the ring (15).

5. A prosthesis as claimed in claim 4, wherein annular shims (19) are provided which can be inserted between the contact surface (5) and the ring (15).

6. A prosthesis as claimed in claim 1, wherein the prosthesis includes a neck part (6) carrying a prosthesis head (7) and the neck part is releasably joined via adapters (14) of adjustable length to the upper portion of the stem (1).

7. A prosthesis as claimed in claim 2, wherein the support means includes a ring, and the interspaces are defined by ribs radiating in the form of a star from the ring (15).

8. A prosthesis as claimed in claim 2, wherein the prosthesis includes a neck part (6) carrying a prosthesis head (7) and the neck part is releasably joined via adapters (14) of adjustable length to the upper portion of the stem (1).

* * * * *